United States Patent [19]

Bondell et al.

[11] Patent Number: 5,074,317
[45] Date of Patent: Dec. 24, 1991

[54] SYSTEM FOR TREATMENT OF ENURESIS

[76] Inventors: James A. Bondell, 5403 Candlelight Dr.; Mark G. Wiesner, 8193 Via Mallorca, both of La Jolla, Calif. 92037; Dennis L. Vories, 29142 Via Piedra, Valley Center, Calif. 92082

[21] Appl. No.: 328,310

[22] Filed: Mar. 24, 1989

[51] Int. Cl.[5] .............................................. A61F 5/48
[52] U.S. Cl. ................................... 128/886; 340/573
[58] Field of Search ................ 128/885, 886; 340/573, 340/604, 575

[56] References Cited

U.S. PATENT DOCUMENTS

| | | | |
|---|---|---|---|
| 2,866,454 | 8/1957 | McKenzie | 128/132 |
| 2,907,841 | 10/1959 | Campbell | 200/61.05 |
| 3,460,123 | 8/1969 | Bass | 340/235 |
| 3,530,855 | 6/1968 | Balding | 128/138 |
| 3,592,195 | 6/1968 | Wagener | 128/295 |
| 3,696,357 | 10/1972 | Kilgore | 340/235 |
| 3,803,579 | 4/1974 | Compton | 340/309.1 |
| 3,810,140 | 5/1974 | Finley | 340/235 |
| 3,818,468 | 9/1972 | Toth et al. | 340/224 |
| 4,106,001 | 6/1977 | Mahoney | 340/604 |
| 4,163,449 | 8/1979 | Regal | 128/138 A |
| 4,212,295 | 5/1978 | Snyder | 128/138 |
| 4,220,142 | 9/1980 | Rosen et al. | 340/575 X |
| 4,320,767 | 3/1982 | Villa-Real | 128/680 |
| 4,356,818 | 11/1982 | Macias et al. | 128/138 A |
| 4,366,873 | 1/1983 | Levy et al. | 177/25 |
| 4,539,559 | 9/1985 | Kelly | 340/573 |
| 4,800,370 | 1/1989 | Vetecnik | 128/886 X |
| 4,851,816 | 7/1989 | Macias | 128/886 X |

FOREIGN PATENT DOCUMENTS

| | | |
|---|---|---|
| 2921655 | 12/1980 | Fed. Rep. of Germany . |
| 2529080 | 12/1983 | France . |
| 1223908 | 4/1986 | U.S.S.R. ............ 128/886 |

Primary Examiner—Robert A. Hafer
Assistant Examiner—Kevin G. Rooney
Attorney, Agent, or Firm—Thomas J. Tighe

[57] ABSTRACT

A programmed computer having an integral speech synthesizer and pre-programmed scripts conducts interactive methods of treating a person suffering from enuresis. The computer, preferably at the bedside of the person being treated, communicates with the person by means of a display panel, a plurality of input keys, and synthesized speech. The computer uses primarily uttered procedural instructions and verbal rewards, such as congratulatory statements, and visual displays to conduct the treatment methods. The person communicates selections and responses to the computer by means of the key. The computer receives RF signals broadcast from two sources: a device for sensing wetness which attaches to the underpants of the person, and a momentary remote key preferably located next to or on a toilet. The signals are encoded to enable the computer to distinguish between the sources. A nocturnal monitoring, treatment and scoring method conducted by the computer uses the wetness sensing device and the remote key to train the person under treatment to awaken when urination is imminent and go to the toilet. Other treatment methods conducted by the computer strengthen the person's urinary sphincter muscles and enlarge the person's bladder capacity. Pre-programmed instructions tutor the user on the proper use of the treatment program, and a game endears the system to the user.

20 Claims, 3 Drawing Sheets ns and
methods for treating persons who suffer from enuresis,
commonly referred to as bed wetting, and urinary incontinence, and in particular to those apparatuses and
methods which utilize interactive control means, remote moisture sensing and remote keying.

The prior art presents moisture sensors for clothing,
diapers, and bedding which sound alarms to arouse a
person from sleep when moisture is detected, such as
U.S. Pat. No. 2,907,841 by Campbell; U.S. Pat. No.
3,530,855 by Balding; and U.S. Pat. No. 3,810,140 by
Finley.

This invention uses an enuretic treatment system for
treating bed wetting. The means and methods of this
invention are interactive with the person being treated.
Some of the methods according to this invention are
designed to communicate particularly with children,
but the device and basic methods are useful to all. So in
this specification and claims which follow the term
"child" shall refer to and mean the person being treated
for enuresis and/or incontinence regardless of the age
of the person.

The treatments are primarily conducted by a programmed bedside computer which communicates to the
person being treated in the forms of synthesized speech
and indicators on a display. Procedural instructions are
issued and verbal rewards are selectively uttered by the
computer. The person being treated communicates selections and responses to the computer by means of a
plurality of keys, the keys and display being parts of an
operator console.

The display serves many functions as will be explained, but its basic function is as a scoreboard calendar. A urination sensor communicates with the computer which maintains a 24-hour clock and calendar.
Wet nights (nights during which the person urinates
involuntarily) and dry nights (no involuntary urination)
are noted and recorded in the morning. When a dry
night is achieved the person is rewarded verbally. If
three consecutive dry nights are achieved the person
receives a material reward from a parent, and a grand
prize is awarded for 15 consecutive dry nights, which is
considered to be a successful completion of the treatment.

Other advantages and attributes of this invention will
be seen from a reading of this specification.

SUMMARY OF THE INVENTION

An object of this invention is to provide a user
friendly, interactive means for treatment of enuresis.

A further object of this invention is to provide a user
friendly, interactive means for treatment of enuresis
which detects urination by a wireless sensor, arouses the
child by some means when urination is detected, and
requires that the child actuate a key remote from the
child's bed, preferably located proximate a toilet facility, to de-activate the arousing means to ensure that the
child gets up and goes to the toilet facility.

A further object of this invention is to provide a
means for treatment of enuresis as described in the preceding paragraph which includes a program for instructing the child through one or more therapeutic
exercises.

A further object of this invention is to provide a
computer driven system for training both the voluntary
and the involuntary urinary sphincter muscles especially for use by persons suffering for enuresis or urinary incontinence, which system uses a combination of
computer generated audio and visual stimuli.

A further object of this invention is to provide a
computer driven system to strengthen a person's urinary sphincter muscles, increase awareness of a full
bladder, and to increase bladder capacity especially for
use by persons suffering for enuresis or urinary incontinence, which system uses a combination of computer
generated audio and visual stimuli.

These and other objects which will be discussed or
which will be apparent from a reading of the text herein
are accomplished by a system for conducting a nocturnal treatment for enuresis comprising a means for sensing when a child has wet his or her underpants and
transmitting a first signal in response thereto, a means
remote from the child's bed, preferably located in a
toilet facility (also referred to herein as a "bathroom"),
for transmitting a second signal when actuated by the
child, means for arousing the child from sleep, said
means being activated by the first signal and de-activated by said second signal, and means for means for
issuing instructions to the child to the effect that the
child should go to the toilet facility and actuate the
means for transmitting the second signal, said instructions being issued in response to the first signal and
terminating in response to the second signal. Preferably
the system further comprises means for recording dry
and wet nights, and means for indicating at least the dry
nights to the person for positive feedback; and means
for instructing the person through at least one therapeutic exercise. Also it is preferable that the system have
the capability of interactively communicating with the
child, e.g., for verbally giving the child instructions,
explanations and verbal rewards, and for receiving responsive inputs from the child. Preferably, a nocturnal
treatment method, including monitoring dry and wet
nights, and one or more therapeutic methods are conducted interactively by a bedside computer which is the
control means for the device of this invention.

As used in this specification, including the claims, the
term "computer" shall refer to any device or machine
capable of accepting information, applying prescribed
processes to the information, and supplying the results
of the processes; and the term "underpants" shall refer
to any garment worn by a person while retired to bed
which will probability become wetted if the person
urinates while wearing it, such as drawers, shorts, panties, and the like usually worn at least in part to cover the
genitalia of the person.

DESCRIPTION OF THE PREFERRED EMBODIMENT

Figure 1:
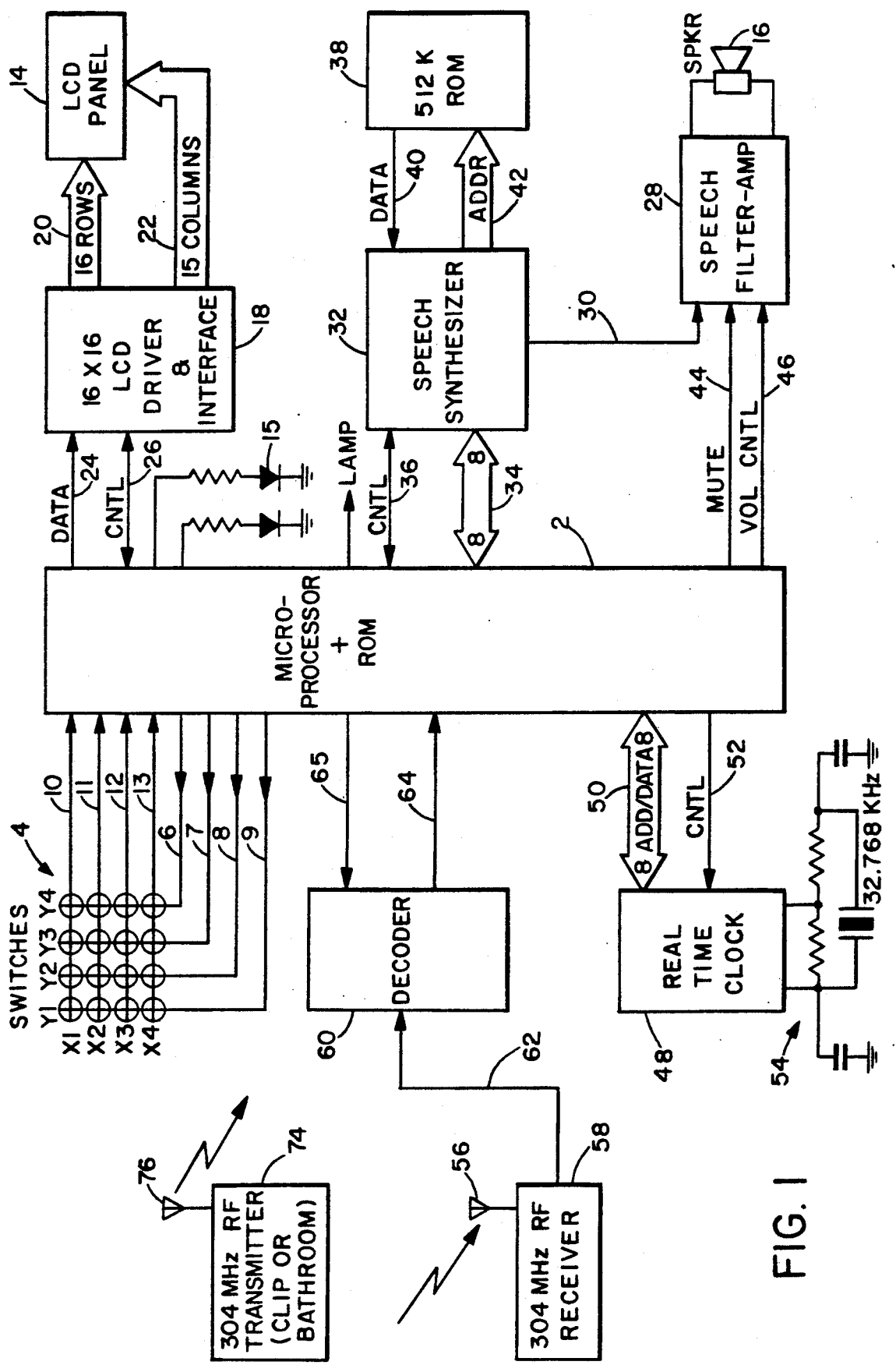
FIG. 1 is a functional block diagram of the bedside
computer, moisture sensor and remote key.

Referring to FIG. 1, a bedside computer comprising a processor 2, preferably a microprocessor such as one of the MC6800 family, with input and output devices (I/0) is functionally illustrated. The processor is shown to have read-only memory (ROM) in which reside the system program and a plurality of programs for directing a child through therapeutic exercises. The processor ROM may be integrated with or external to the processor. The processor 2 receives operator (usually the child) input from a matrix of sixteen switches or keys generally designated 4, the matrix being illustrated as having four rows, X1-X4, and four columns, Y1-Y4. In operation when the processor is scanning the keys, the columns are sequentially energized by the processor via lines 6-9, and while each column is so energized the rows are sequentially sensed by the processor for the presence of energization via lines 10-13. A key actuation, i.e., a key closure is sensed whenever its column is energized and the key is closed while its row is being sensed for energization by the processor.

Referring again to FIG. 1, the processor communicates information to the operator by means of a liquid crystal display (LCD) panel 14, light emitting diodes 15, and an audio speaker 16. The LCD panel comprises 240 segments of liquid crystal material organized electrically and generally physically into 16 rows and 15 columns. The molecular orientation of the liquid crystal material of the segments is controlled by an LCD driver and interface circuit 18 via sixteen row control lines 20 and fifteen column control lines 22. The LCD driver and interface circuit receives serial data from the processor via data line 24, and receives control signals from, and communicates an interrupt signal to, the processor via control lines 26.

Referring again to FIG. 1, the speaker 6 is driven by a speech filter and amplifier circuit 28 which receives a speech signal 30 from a speech synthesizer 32, such as a TSP5220C. The processor and speech synthesizer 32 communicate data bi-directionally, i.e., to each other, via data lines 34, and they communicate control signals via control lines 36. The speech synthesizer receives patterns in the form of a plurality of sets of digital data from a pre-programmed speech ROM 38 via data lines 40 in response to addresses sent to the speech ROM by the speech synthesizer via address lines 42. The processor controls the volume level and muting of sound being emitted from the speaker via a mute signal line 44 and volume control signal lines 46, all of which communicate their respective signals from the processor to the speech filter and amplifier circuit 28 in which there are circuits for muting and volume control.

Referring again to FIG. 1, the system also has a real time clock and calendar circuit 48, such as an MC146818, which communicates data to the processor and receives addresses from the processor via a bi-directional address/data bus 50. The real time clock and calendar 48 also receives control signals including a reset signal from the processor via control lines 52. An external circuit generally designated 54 cooperates with a circuit internal to the real time clock to form an oscillator to generate a time base, the external circuit comprising passive elements and a piezoelectric crystal, illustrated to be cut to have a fundamental frequency of 32.768 KHz.

Referring again to FIG. 1, the bedside computer, during certain procedures as will be explained hereinafter, receives one or the other of two radio frequency (RF) signals which are broadcast from two separate sources: a moisture sensor and a remote key. The RF signals each comprise a burst of digital information distinctly encoded. The RF signals are sensed by an antenna 56 in communication with an RF receiver circuit 58 which conditions the signals by detecting, amplifying and filtering them. The conditioned signals are then communicated to a decoder circuit 60, such as an MC145028, via signal line 62. The decoder circuit compares the conditioned signals to a preset code and communicates a signal to the processor via signal line 64 when there is a match. The preset code is alterable between two states by a bi-polar signal communicated from the processor to the decoder via signal line 65. Preferably the state of said signal line determines the presence or absence of a single bit of the preset code. In this way the processor selectively conditions the decoder to recognize either the moisture sensor code or the remote key code.

Referring again to FIG. 1, the two sources of the RF signals are shown collectively as one functional block 74 with antenna 76 because their RF transmitting circuits are identical, but they are individual and separate units, and perform separate functions. "Clip" refers to the moisture sensor which is in the form of a clip having jaws biased closed As will be further explained hereinafter, the jaws and an adjacent rivet form electrodes which are fastened to a portion of the underpants that will be moistened if the child involuntarily urinates. "Bathroom" refers to the remote key which is preferably located in a bathroom, i.e., a toilet facility. Moisture causes the moisture sensor to transmit, and physical actuation by the child causes the remote key to transmit. Both are illustrated as transmitting at a frequency of 304 MHz, but as explained above, they are distinguished by their distinct digital coding.

Figure 2:
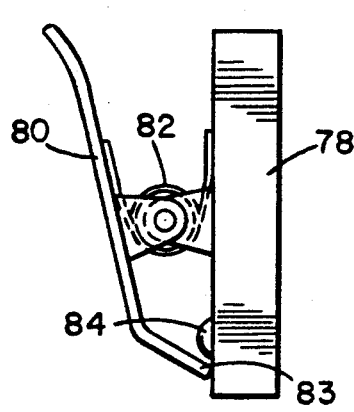
FIG. 2 is a side view of the moisture sensor.
Figure 3:
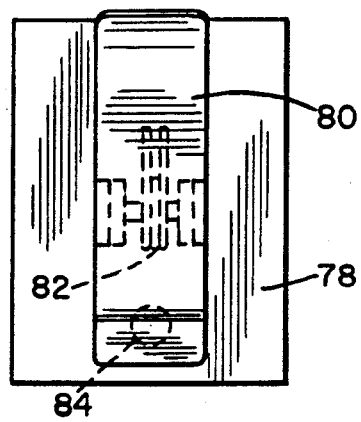
FIG. 3 is a rear view of the moisture sensor.
Figure 4:
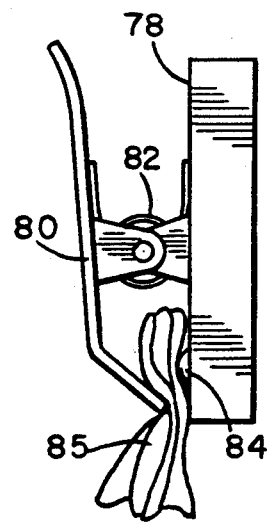
FIG. 4 is a side view of the moisture sensor clipped to
a child's underpants.

Referring to FIGS. 2-4, an encasement 78 containing the moisture sensor circuit has pivotally affixed to it a jaw 80. A spring 82 biases the jaw closed against the encasement. A rivet 84 protrudes from the encasement and faces the jaw 80, but the rivet is disposed so that the jaw never touches the rivet. FIG. 2 illustrates a gap 83 between the jaw and rivet when the jaw is closed against the encasement. The jaw, spring and encasement cooperate to form a clip by which the moisture sensor is attached to a child's underpants 85 by pinching the fabric of it. The jaw is forced apart from the encasement to fasten to the crotch of underpants of a child's bedclothes. Preferably the underpants are jockey or panty style, i.e., underpants which are snug against the child's crotch. In operation the moisture sensor is clipped to the fabric in a fashion to ensure that the fabric bridges the gap between the jaw and the rivet and at a location which ensures that the pinched fabric will be wetted whenever the child involuntarily urinates.

Figure 5:
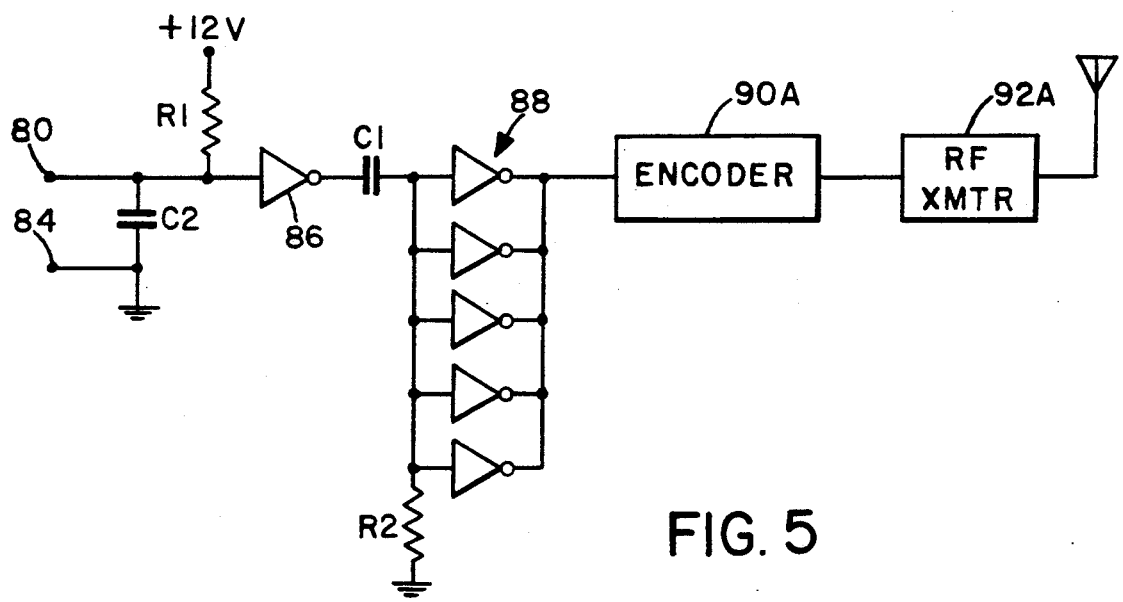
FIG. 5 is a schematic diagram of the moisture sensor.

Referring to FIG. 5, the jaw 80 and rivet 84 are illustrated to be electrodes, one being connected to an electrical ground reference and the other being in electrical communication with a filter comprising a 100K ohm resistor R1 in series with a 10 microfarad capacitor C2, the resistor end of the filter being connected to supply voltage, in this case 12 volts, and the capacitor end of the filter being connected to the ground reference. R1 and C2 form a low-pass filter delay circuit to prevent accidental retriggering of the moisture sensor RF signal when the sensor unit is being unclipped from wet underpants. An invertor 86 has its input in communication with the output of the low pass filter taken between R1 and C2. The output of the invertor 86 communicates with a high-pass filter comprising a 10 microfarad capacitor C1 in series with a 330K resistor R2 to ground. The output of the filter taken between the capacitor C1 and resistor R2 communicates with the inputs of a bank 88 of five invertors all connected in parallel to form a power amplified pulse generator. Preferably the invertors are all part of a Schmitt-trigger CMOS hex invertor generically designated 40106. The output of the invertor bank 88 communicates with an encoder 90A (preferably an MC145026) and an RF transmitter 92. The pulse generator functions as an electronic switch causing operation of the encoder and RF transmitter.

In operation, when a child wets his or her underpants including the portion 85 being pinched between the jaws, the moisture will provide a path of very low electrical impedance, relative to R1, between the jaw and rivet and will essentially short the input of the invertor 86 to ground. The output of the invertor 86 will then go to a logic high, which will be very close to supply voltage. Prior to the wetting the dry fabric between the jaws offered only a high impedance (relative to R1) path and the output of the invertor 86 was at a logic low, very close to ground. The logic high at the output of the invertor 86 will be felt at the input of the invertor bank the output of which will then switch from a logic high to a logic low. The condition will persist until the capacitor C1 charges to a point past the input switching threshold of the bank, the output of which will then return to a logic low. It can be seen, therefore, that the wetting causes a single low going pulse to be emitted by the invertor bank 88.

Figure 6:
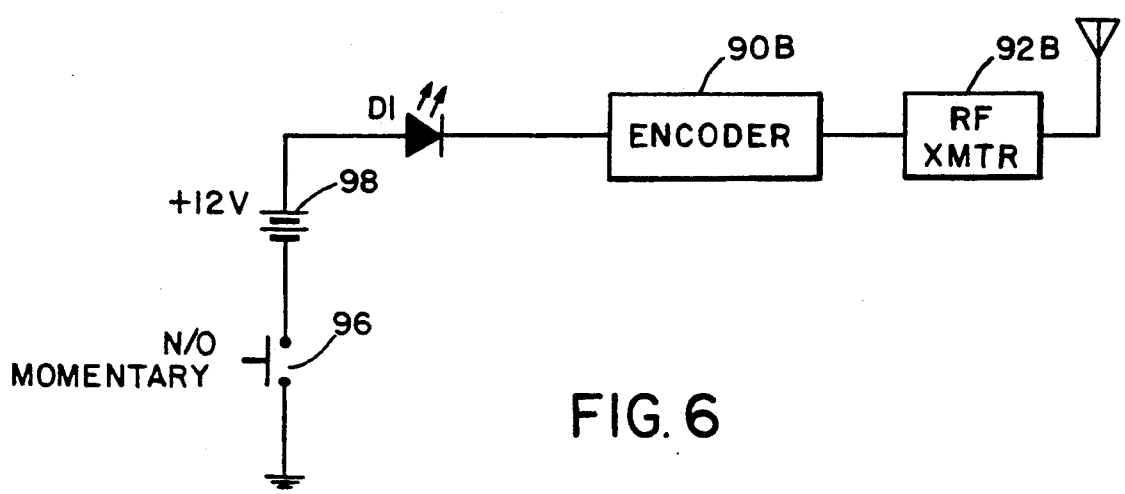
FIG. 6 is a schematic diagram of the remote key.

Referring to FIG. 6, the remote key circuit comprises a normally-open momentary switch 96 which when actuated provides a ground reference for the remote key circuit causing it to be energized by a 12 volt battery power source 98. The switch 96 also provides a 12 volt signal at the input of an encoder 90B which is preferably identical to the moisture sensor encoder 90A but programmed to produce a digital code separate and distinct from the code produced by encoder 90A. The digital code produced by the encoder 90B is communicated to an RF transmitter 92B which is preferably identical to the moisture sensor transmitter 92A since they both transmit at the same frequency of 304 MHz. A light emitting diode D1 in series with the circuit illuminates when the circuit is energized to indicate correct actuation of the remote key and good battery condition.

Figure 7:
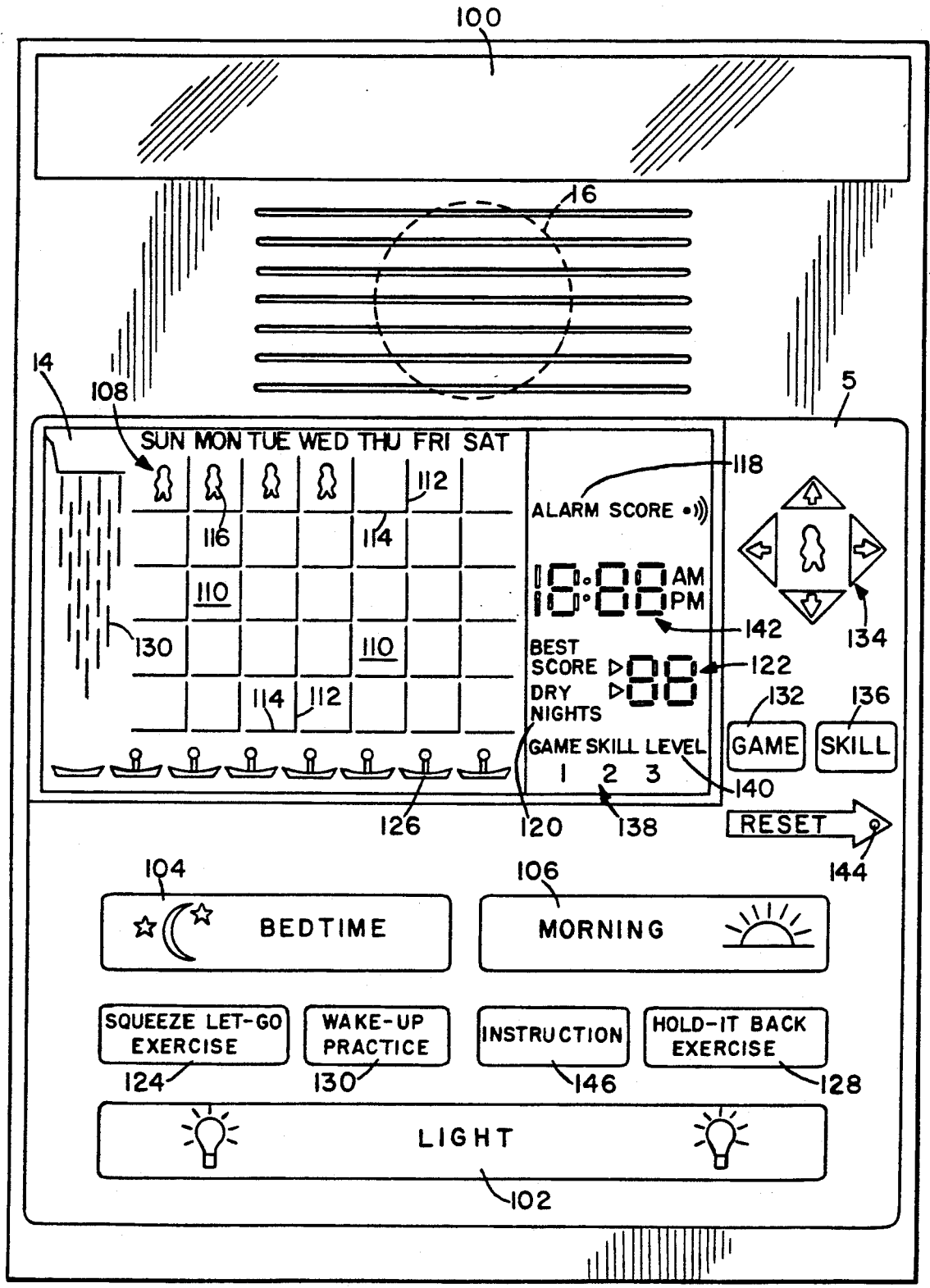
FIG. 7 is a plan view of the bedside computer.

Referring to FIGS. 1 and 7, an operator's console of the bedside computer is illustrated as comprising the previously referenced LCD panel 14 having a plurality of indicia and a key panel 5 having the keys 4 for operator input. A lamp 100 is turned on and off by actuation of a "Light" key 102, but it is automatically illuminated by the bedside computer as will be explained hereinafter. A speaker 16 is used by the bedside computer to emit audible sounds the volume of which is controlled by a volume control (not shown) located beneath a removable cover for the lamp 100. A "Bedtime" key 104 is actuated by the child primarily to initiate and setup a nocturnal monitoring and treatment method, the termination of which is caused by actuation of a "Morning" key 106.

Referring again to FIG. 7, a portion of the LCD panel 14 is a scoreboard display, generally designated 108, comprising a five row by seven column matrix of generally square cells 110, each cell being defined by at least one vertical LCD line segment 112 and one horizontal LCD line segment 114. Centrally disposed in each cell is an LCD indicia 116 representing a persona which preferably the child is made to perceive as friendly and helpful by use of the game as hereinafter described. All of the indicia and line segments can be selectively made opaque, i.e., visible, or transparent, i.e., invisible, by the bedside computer. The columns of the scoreboard are labeled by abbreviations for the days of the week from Sunday through Saturday, so five consecutive weeks are represented, each row representing a week and each cell in a row representing a night of its respective week. As will be further explained, the bedside computer uses the scoreboard for various display functions but its primary function is to indicate the child's consecutive nighttime history, whether dry or wet, for up to a five week period. For those nights that were dry the bedside computer makes the friendly persona indicia in the cells representing those nights visible, but the friendly persona indicia in the cells representing nights that were wet remain invisible. When the scoreboard becomes filled, i.e., five consecutive weeks have elapsed, the bedside computer scrolls the scoreboard contents upward to empty the bottom row but preserve the history of the previous four weeks.

Referring again to FIG. 7, a nocturnal treatment method, including monitoring of dry and wet nights, for training a child to awaken and go to the bathroom when he or she feels the need to urinate comprises the following steps: (a) actuating, i.e., pressing the Bedtime key at the bedtime of the child being treated for keying the computer to initiate the nocturnal monitoring and treatment method; (b) in response to said keying of the Bedtime key, issuing verbal instructions to the child by means of the bedside computer to the effect that the child should go to a toilet facility and urinate if the child feels the need, for example the bedside computer may utter, "If you have to go to the bathroom, go now," and to key the computer by re-actuating the Bedtime key, said re-actuation being an acknowledgment to the bedside computer that the child has either returned from the bathroom or had no need to go; (c) upon the keying of the computer by the re-actuation of the Bedtime key in the previous step, issuing verbal instructions to the child by means of the bedside computer to the effect that the child should attach the urination sensor to his or her dry underpants and to re-actuate the Bedtime key, said re-actuation being an acknowledgment to the bedside computer that the child has so attached the wetness sensor, the child having previously been coached to attach the sensor at a location which will become wetted if the child urinates; (d) if the child thereafter involuntarily urinates while wearing his or her underpants and as a result wets the underpants, sensing the wetness by means of a wetness sensor and communicating that fact to the bedside computer, for example, by broadcasting a pulse or burst of a first digitally encoded RF signal via the wetness sensor RF transmitter 92A (see FIG. 5) which signal is detected by the RF receiver 58 (see FIG. 1) of the bedside computer; (e) if the bedside computer detects a transmission from the wetness sensor that the underpants are wet, sounding an alarm, preferably a combination of a tone and verbal commands (e.g., "Squeeze! Hold Back! Wake up! Wake up!") emitted by the bedside computer which get progressively louder for waking the child, said commands comprising at least an instruction to the effect that the child should immediately go to the bathroom and actuate the remote key 96 (see FIG. 6); (f) when the remote key is actuated, communicating that fact to the bedside computer, for example, by broadcasting a second digitally encoded RF signal for the duration of the actuation via the RF transmitter 92B (see FIG. 6) which signal is detected by the RF receiver 58 (see FIG. 1) of the bedside computer; (g) when the bedside computer detects a transmission from the remote key that it has been actuated, ceasing the sounding of the alarm and issuing verbal instructions to the child to the effect that the child should re-actuate the Bedtime key, said re-actuation being an acknowledgment to the computer that the child has returned from the bathroom; (h) upon the keyed acknowledgment of the previous step, issuing further instructions to the child by means of the computer to the effect that the child should take remedial action concerning the wetness of his or her bedclothes and bedding, for example, change bedclothes and sheets, and thereafter to return to bed; (i) when the child awakens in the morning, keying the computer by actuating the Morning key, said keying being a communication to the computer that the child has awakened; and (j) if the child had a dry night, that is, the child did not involuntarily urinate and wet his or her underpants, rewarding the child, for example by verbal congratulations uttered by the bedside computer, (such as, "Congratulations, you had a dry night."); or if there have been consecutive dry nights, verbally indicating by means of the bedside computer the number of such nights, for example the bedside computer may utter, "You now have 5 dry nights in a row."

The nocturnal monitoring and treatment method may include additional steps to provide the child with a bedside light before and as the child retires, such as: (a) when the bedside computer is keyed to initiate the method energizing the lamp 100 by means of the computer to provide light for the child; (b) later on issuing verbal instructions by means of the computer to the effect that the child should key an acknowledgment when said child is retiring to bed, such as after the child has keyed an acknowledgment to the computer that he or she has attached the wetness sensor; and (c) following the acknowledgment that the child is retiring, extinguishing the lamp, or if the child fails to so acknowledge, extinguishing the lamp after a length of time, for example twenty minutes.

The nocturnal monitoring and treatment method may also include the step of issuing a reminder by means of the computer of the sounds that the computer will create to awaken the child if he or she should wet during the night. Preferably the reminder is issued immediately after the child has acknowledged that he or she has attached the wetness sensor. For example the computer may inform the child that if he or she wets, then the computer will utter, "Squeeze! Hold Back! Wake up, wake up! Get up and go to the bathroom and press my bathroom switch." The computer may also concurrently sound a tone which can additionally be used to awaken the child.

The nocturnal monitoring and treatment method may also include the steps of making the alarm indicia 118 visible, informing the child that the alarm is set and uttering words to the effect of wishing the child a dry night, all by means of the computer, following the child's keyed acknowledgment that he or she is retiring to bed. Preferably the lamp 100 is extinguished after these steps.

The nocturnal monitoring and treatment method may further comprise steps to provide the child with bedside light when the child is aroused during the night by the computer because of wetting, such as: (a) energizing the lamp by means of the computer concurrent with creating the sounds to awaken the child following the computer's detection of a transmission from the wetness sensor; (b) after the child has acknowledged his or her return from the bathroom, issuing verbal instructions by means of the computer to the effect that the child should key an acknowledgment when the child is returning to bed; and (c) following the acknowledgment that the child is returning to bed, extinguishing the lamp, or if the child fails to so acknowledge, extinguishing the lamp after a length of time suitable to allow the child sufficient time to remedy the wetness and return to bed.

The computer can also conduct, i.e., lead the child through, therapeutic methods designed to improve the child's bladder control. Referring again to FIG. 7, one such therapeutic method, herein called the "Squeeze Let-Go Exercise" for reference purposes only, can be practiced by the child under treatment to strengthen the child's voluntary and involuntary urinary sphincter muscles. The Squeeze Let-Go treatment method comprises the steps: (a) actuating the "Squeeze Let-Go Exercise" key 124 which keys the computer to initiate the method; (b) informing the child by means of the bedside computer that the method is about to begin, for example the bedside computer may utter, "Now let's do your Squeeze Let-Go exercise;" (c) issuing verbal instructions to the child by means of the bedside computer to the effect that the child should squeeze, i.e., contract, the child's urinary sphincter muscles; (d) issuing verbal instructions to the child by means of the bedside computer to the effect that the child should hold the urinary sphincter muscles in the contracted state, for example, by a series of "Hold back!" commands; (e) issuing verbal instructions to the child by means of the bedside computer to the effect that the child should let go, i.e., release, the child's urinary sphincter muscles; (f) repeating steps (c) through (e) a plurality of times, preferably fourteen more times; (g) praising the child by means of the bedside computer for having performed the method. The Squeeze Let-Go method may further comprise steps to provide a visual display to aid the child in practicing said method, such as: (h) upon initiation of the method, filling the scoreboard 108 with an array of visible personae 116; (i) sequentially reducing the size of the array in an inwardly shrinking fashion during steps (c) and (d); (j) sequentially increasing the size of the array in an outwardly expanding fashion during step (e); and (k) restoring the scoreboard to its original configuration with respect to visible personae after the conclusion of step (f). As the child is instructed to squeeze his or her sphincter muscles the child sees the full scoreboard of personae shrink in steps to one centrally disposed persona, and as the child is instructed to let go the child sees the personae expand in steps from the one to again fill the scoreboard, the shrinking and expanding of the personae array simulating to the child what the child is doing to the opening of the child's urinary sphincter.

The nocturnal monitoring and treatment method described above may further comprise the step of leading the child by means of the computer through a therapeutic method, such as the Squeeze Let-Go Exercise method, to enhance the child's control over his or her urinary system. Preferably the computer instructs the child to practice the therapeutic method each night at a point after initiation of the nocturnal monitoring and treatment method but before the child retires to bed. For example, after the child has keyed the acknowledgment that he or she has either returned from the bathroom or had no need to go (step (b) of the nocturnal monitoring and treatment method) and prior to instructing the child to attach the wetness sensor (step (c)), the computer may initiate the Squeeze Let-Go exercise on its own and lead the child through it. In such case the acknowledgment that the child would key to indicate that he or she has attached the wetness sensor (step (c) of the nocturnal monitoring and treatment method) would also be an acknowledgment that the child has performed the therapeutic method.

The nocturnal monitoring and treatment method may further comprise additional morning steps as follows: (a) after the child has awakened and has informed the computer of that fact by keying the Morning key, issuing verbal instructions by means of the computer to the effect that the child should go to a toilet facility and urinate if the child feels the need and to key an acknowledgment to the computer that he or she has either returned from the bathroom or had no need to go; and (b) leading the person by means of the computer through a therapeutic method to enhance the person's control over his or her urinary system, for example the computer may initiate the Squeeze Let-Go Exercise method on its own and lead the child through it, followed by a keyed acknowledgment that the child has performed the therapeutic method.

The morning "rewarding" step of the nocturnal monitoring and treatment method (step (j)) is to provide the child with positive feedback if the child has had a dry night and may comprise the steps: (j.1) congratulating the child and telling the child the number of consecutive dry nights by computer utterances (for example, "Congratulations! You had a dry night. You proved you can do it. You now have five dry nights in a row.") preferably right after the child first actuates the Morning key; or (j.2) updating numerical indicia displayed by the computer to show the person his or her current total of consecutive dry nights, such as making visible a "DRY NIGHTS" indicia 120 of the LCD panel 14 and displaying the number of consecutive dry nights on a numerical display 122 portion of the panel; or (j.3) updating a calendar indicia displayed by the computer to show the person calendar-wise his or her current total of consecutive dry nights, such as updating the scoreboard display 108 by making the friendly persona indicia 116 in the cell 110 representing the previous night visible; or (j.4) rewarding the person by things given to him or her by another person; or (j.5) any combination thereof. Moreover, for certain totals of consecutive dry nights, such as one, two, four, five, seven, eight, ten, eleven, thirteen or fourteen consecutive dry nights, the verbal utterances of step (j.1) can be proceeded by having the computer emit a tune or jingle which the child will associate with success; and for certain other totals of consecutive dry nights, such as three, six, nine, twelve or fifteen consecutive nights, the jingle of success can be accompanied by computer simulated applause and/or by a flashing of the lamp 100 and the entire display 180 degrees out of phase at a 1 Hz rate, and a tangible reward. Preferably on the morning of the fifteenth consecutive dry night the therapeutic exercise is omitted because the child is considered to be cured, and the child is given a grand prize. Preferably the morning messages are available between 3 AM and noon of the following day, and the scoreboard display is updated in response to the Morning key being actuated or at noon of the following day, whichever occurs first.

All of the methods and procedures of this invention can have additional steps wherein each of the acknowledgment keys which the child is instructed to actuate during various steps is flashing lighted, e.g. at a rate of 2 Hz, when the child is expected to key it and not at other times.

Referring again to FIG. 7, the LCD panel 14 further comprises a plurality of LCD indicia 126 each representing a child in a canoe, the indicia being arranged in a horizontal row beneath the scoreboard 108. Each of the child-in-canoe indicia 126 can be selectively made opaque, i.e., visible, or transparent, i.e., invisible, by the bedside computer. One function of said indicia is to indicate how many times the child has practiced the Squeeze Let-Go method in a day, the number of indications being limited to the number of child-in-canoe indicia (FIG. 7 illustrating seven such indicia). At the end of each Squeeze Let-Go exercise the bedside computer adds one more visible child-in-canoe indicia up to said limit. At a suitable time each night the child-in-canoe display is cleared.

Referring again to FIG. 7, another therapeutic method, herein called the "Hold-It-Back Exercise" for reference purposes only, can be practiced by the child under treatment to strengthen the child's urinary, sphincter muscles, increase the child's awareness of a full bladder, and to increase the child's bladder capacity. The Hold-It-Back treatment method comprises the steps: (a) actuating the "Hold-It-Back Exercise" key to initiate the method at least once a day when the child under treatment feels the need to urinate; (b) verbally acknowledging to the child by means of the bedside computer that the child is feeling a need to go to the bathroom to urinate, for example the bedside computer may utter, "I know you have to go to the bathroom;" (c) initially clearing the scoreboard 108 of visible personae 116 by means of the computer; (d) issuing verbal instructions to the child by means of the bedside computer to the effect that the child should refrain from going to the bathroom as long as the child can or until the scoreboard is full of visible personae, for example the bedside computer may utter, "Now hold it back as long as you can or until you have filled the scoreboard," and then go to the bathroom and actuate the remote key; (e) periodically adding by means of the computer a visible persona to the scoreboard at a corner of the scoreboard and advancing previously added visible personae cell by cell and row by row across the scoreboard such that, after a number of periods equal to the number of scoreboard cells, the scoreboard will be full of visible personae, until either the computer receives a transmission from the remote key or the scoreboard is full; (f) if the scoreboard becomes full of personae indicia, congratulating the child and issuing verbal instructions to the child by means of the bedside computer to the effect that the child should go to the bathroom and actuate the remote key; and (g) upon actuation of the remote key, maintaining the personae configuration of the scoreboard long enough to enable the child to return to the bedside computer and see how well he did, for example, ten minutes. Optionally, each time the child is able to fill the scoreboard, the bedside computer will remember that fact, and the next time the child practices the method, the bedside computer will increase the time it takes to fill the scoreboard, for example by seventy seconds, to provide an increased challenge for the child up to a safe limit.

Referring again to FIG. 7, along the left-hand margin of the LCD panel 14 is a plurality of LCD line segments vertical oriented and arranged to represent a waterfall 130. One function of the waterfall indicia is to indicate that the child has completed the Hold-It-Back exercise method at least once during the current day, and at the conclusion of said method, the bedside computer will for ten minutes selectively make the LCD segments comprising the waterfall visible and invisible to give it an actively flowing appearance. Afterward it will be become steady and remain so until 3:00 AM the next morning at which time the computer will clear the waterfall display.

Referring again to FIG. 7, a child can practice that portion of the nocturnal monitoring and treatment method which comes into play when the child involuntarily urinates. The practice is for conditioning the child to respond correctly to the alarm. This practice is initiated by actuating a "Wake-up Practice" key 130 while the child pretends he or she is asleep. The bedside computer then sounds the alarm and issues instructions as in steps 7 through 12 of the nocturnal monitoring and treatment method as explained above.

Referring again to FIG. 7, the operator's console has a number of indicators and keys associated with a game the child can play with the bedside computer. The game is designed to improve hand-eye coordination, to help the child become comfortable with the bedside computer, and to endear the child to the treatment program. The object of the game is to move a persona down a steep cliff through a maze to rescue a child asleep in a canoe who is drifting toward a waterfall. The game is initiated by actuation of a "Game" key 132. The persona of the game is the friendly persona represented by the indicia 116. Initially a persona in the top row of the scoreboard is made visible. Movement of the persona over the scoreboard is controlled by the child through selective actuations of direction keys 134. There are four direction keys for movement of the persona up, down, left and right, and each direction key is marked by an arrow pointing in the direction that the persona moves when the key is actuated. The bedside computer makes the persona appear to move in a direction indicated by the arrow on a currently actuated direction key by selectively clearing and making visible personae indicia in adjacent cells in line with said direction. The maze comprises a pattern of vertical and horizontal walls which block movement of the persona in the direction of the walls. Each wall is simulated by visible line segments, 112 and/or 114. At the start of the game the right two digits of a first numerical display 142 is set at its maximum which is ninety nine. During the game the first numerical display is periodically decremented until it reaches zero. The waterfall indicia 130 is made to appear flowing during the game and the child-in-canoe indicia 126 without the child portions are selectively made visible to give the appearance of a sleeping child (not seen) in a canoe moving toward the waterfall. The movement of the canoe and the decrementing of the numerical display are coordinately timed such that as the canoe reaches the waterfall the first numerical display 142 reaches zero and the game ends. The playing child tries to move the persona directly above the canoe before it reaches the waterfall, i.e., the currently visible canoe, and actuate the down direction key before the canoe moves on. If the child is successful, the computer utters statements simulating an attempt to awaken the child in the canoe, such as, "Wake up, Wake up," and the computer then makes the child portion of the child-in-canoe indicia visible which gives the appearance of a child sitting up in the canoe. At that point the game ends. The child's score is the value in the numerical display at the time the game ends. The best game score attained at any time during the treatment program is displayed by the two digits of a second numerical display 122 along with illumination of a "BEST SCORE" indicium. (Note that these same two digits of the second numerical display 122 serve as a count down indicator, from fifteen to zero, during the Squeeze Let-Go Exercise.) There are three skill levels which can be selected and entered at the beginning of the game by means of a "Skill" key 136. The skill level selected by the child is indicated on the LCD panel 14 by the visibility of one of three number indicia 138 below a "Game Skill Level" indicia 140. Level one has a fixed maze, at level two the maze is changed several times during the game, and at level three the maze is changed more frequently.

Referring again to FIG. 7, the first numerical display 142 normally displays the time of day which is kept by the real time clock 48 (see FIG. 1). The time of day and calendar kept by the real time clock are set by selective actuation of the direction keys 134 following a reset which occurs when a "Reset" key 144 is actuated, normally when the bedside computer is first being set up, or when there has been a power loss. The Reset key is a pen key to avoid inadvertent actuation. An "Instruction" key 146 is actuated when an operator wishes to obtain detailed verbal instructions about how to use the bedside computer and implement the treatment program.

The foregoing description and drawings were given for illustrative purposes only, it being understood that the invention is not limited to the embodiments disclosed, but is intended to embrace any and all alternatives, equivalents, modifications and rearrangements of elements falling within the scope of the invention as defined by the following claims.

We claim:

1. A system for conducting a nocturnal treatment for enuresis comprising:
   (a) means for sensing when a person under treatment has urinated and for transmitting a first signal in response thereto,
   (b) means disposed at or near a toilet facility for transmitting a second signal when actuated by the person,
   (c) means for arousing the person from sleep and urging the person to travel to the toilet facility to actuate the means for transmitting the second signal, the arousing and urging means being activated by the first signal and de-activated by said second signal, and
   (d) means for selectively instructing the person through at least one therapeutic physical exercise designed to enhance the person's control over his or her urinary system.

2. The system of claim 1 further comprising indicative means for providing positive feedback to the person at least following dry nights.

3. The system of claim 1 further comprising means for selectively conducting the person through an exercise which simulates the conduct of the system when the person nocturnally involuntarily urinates for conditioning the person to respond correctly to the means for arousing the person from sleep and urging the person to travel to the toilet facility.

4. The system of claim 1 further comprising selectively activated means for conducting an interactive game with the person aimed at endearing the person to the system.

5. A nocturnal treatment method for enuresis comprising the following steps:
(a) keying a computer at the bedtime of a person being treated to initiate said method, said computer being adapted to create humanly audible sound at least in the form of synthesized speech;
(b) in response to said keying, issuing verbal instructions by means of the computer to the effect that said person should go to a toilet facility and urinate if said person feels the need and to key an acknowledgment to the computer that said person has either returned from the bathroom or had no need to go;
(c) following the acknowledgment keyed in step (b), issuing verbal instructions by means of the computer to the effect that said person should attach a wetness sensor to his or her dry underpants and to thereafter key an acknowledgment to the computer that said person has so attached the wetness sensor;
(d) if said person thereafter wets his or her underpants, sensing the wetness by means of the wetness sensor, and communicating the fact of the wetness to the computer by a signal transmission means associated with the wetness sensor and a signal receiving means associated with the computer;
(e) if the computer detects a transmission from the wetness sensor that the underpants are wet, creating sound to awaken the person, said sound comprising at least an instruction to the effect that said person should immediately go to a bathroom in which a remote momentary keying means is located and actuate said remote keying means;
(f) when the remote keying means is actuated, communicating the fact of the actuation to the computer by a signal transmission means associated with the remote keying means and a signal receiving means associated with the computer;
(g) when the computer detects a transmission from the remote keying means that the remote keying means has been actuated, ceasing the sound and issuing verbal instructions to the effect that said person should key an acknowledgment to the computer that said person has returned from the bathroom;
(h) following the acknowledgment keyed in step (g), issuing further instructions by means of the computer to the effect that said person should take remedial action concerning the wetness of said person's bedclothes and bedding, and thereafter return to bed;
(i) when said person awakens in the morning, keying an acknowledgment to the computer that said person has awakened; and
(j) if said person had a dry night, that is, said person did not wet the garment to which the wetness sensor is attached, rewarding said person.

6. The nocturnal treatment method according to claim 5 further comprising the step of leading the person by means of the computer through a therapeutic method after initiation of the nocturnal treatment method but before the person retires to enhance the person's control over his or her urinary system.

7. The nocturnal treatment method according to claim 6 wherein the therapeutic method comprises the steps:
(a) informing said person by means of computer utterances that the method is about to begin;
(b) issuing verbal instructions by means of the computer to the effect that said person should squeeze, i.e., contract, said person's urinary sphincter muscles;
(c) issuing verbal instructions by means of the computer to the effect that said person should hold the urinary sphincter muscles in the contracted state;
(d) issuing verbal instructions by means of the computer to the effect that said person should let go, i.e., release, said person's urinary sphincter muscles; and
(e) repeating steps (b) through (d) a plurality of times.

8. The nocturnal treatment method according to claim 7 wherein the therapeutic method further comprises the steps:
(f) upon initiation of the therapeutic method, filling a display means controlled by the computer with an array of visible indicia;
(g) sequentially reducing the size of the array in an inwardly contracting fashion during steps (b) and (c) to simulate the contraction of the sphincter muscles; and
(h) sequentially increasing the size of the array in an outwardly expanding fashion during step (d) to simulate the release of the sphincter muscles.

9. The nocturnal treatment method according to claim 7 wherein the therapeutic method is conducted as part of step (c) of the nocturnal treatment method before the acknowledgment keyed in said step.

10. The nocturnal treatment method according to claim 5 further comprising the steps:
(a.1) in response to the keying of the computer in step (a), energizing a lamp by means of the computer to provide a light for the person;
(c.1) following the acknowledgment keyed in step (c), issuing verbal instructions by means of the computer to the effect that the person should key an acknowledgment when said person is retiring to bed;
(c.2) following the acknowledgment keyed in step (c.1) extinguishing the lamp; and
(c.3) if the person fails to key an acknowledgment as described in step (c.1) after a selected time, extinguishing the lamp.

11. The nocturnal treatment method according to claim 10 wherein step (c.1) further comprises the step of issuing a reminder by means of the computer of the sounds that the computer will create to awaken the person according to step (e).

12. The nocturnal treatment method according to claim 10 wherein step (c.2) further comprises the steps of making an alarm indicia visible and uttering words to the effect of wishing the person a dry night, both by means of the computer.

13. The nocturnal treatment method according to claim 5 wherein step (e) further comprises the step of energizing the lamp, and step (h) further comprises the steps:

(h.1) issuing verbal instructions by means of the computer to the effect that the person should key an acknowledgment when the person is returning to bed;

(h.2) following the acknowledgment keyed in step (h.1) extinguishing the lamp; and (h.3) if the person fails to key an acknowledgment as described in step (h.1) after a selected time, extinguishing the lamp.

14. The nocturnal treatment method of claim 5 wherein step (j) further comprises the steps of issuing verbal instructions by means of the computer to the effect that the person should go to a toilet facility and urinate if said person feels the need and to key an acknowledgment to the computer that said person has either returned from the bathroom or had no need to go, and leading the person by means of the computer through a therapeutic method to enhance the person's control over his or her urinary system.

15. The nocturnal treatment method according to claim 14 wherein the therapeutic method comprises the steps:

(a) informing said person by means of computer utterances that the method is about to begin;

(b) issuing verbal instructions by means of the computer to the effect that said person should squeeze, i.e., contract, said person's urinary sphincter muscles;

(c) issuing verbal instructions by means of the computer to the effect that said person should hold the urinary sphincter muscles in the contracted state;

(d) issuing verbal instructions by means of the computer to the effect that said person should let go, i.e., release, said person's urinary sphincter muscles; and (e) repeating steps (b) through (d) a plurality of times.

16. The nocturnal treatment method according to claim 15 wherein the therapeutic method further comprises the steps:

(f) upon initiation of the therapeutic method, filling a display means controlled by the computer with an array of visible indicia;

(g) sequentially reducing the size of the array in an inwardly contracting fashion during steps (b) and (c) to simulate the contraction of the sphincter muscles; and (h) sequentially increasing the size of the array in an outwardly expanding fashion during step (d) to simulate the release of the sphincter muscles.

17. The nocturnal treatment method of claim 5 wherein the morning rewarding of step (j) comprises the steps:

(j.1) uttering congratulatory words to the person by the computer and telling the person the number of consecutive dry nights; or (j.2) updating numerical indicia displayed by the computer to show the person his or her current total of consecutive dry nights; or (j.3) updating a calendar indicia displayed by the computer to show the person calendar-wise his or her current total of consecutive dry nights; or (j.4) rewarding the person by things given to him or her by another person; or (j.5) any combination thereof.

18. A first therapeutic treatment method for practice by a person to strengthen said person's urinary sphincter muscles comprising the steps:

(a) keying a computer to initiate said method, said computer being adapted to create humanly audible sound at least in the form of synthesized speech;

(b) in response to said keying, informing said person by means of the computer utterances that the method is about to begin;

(c) issuing verbal instructions by means of the computer to the effect that said person should squeeze, i.e., contract, said person's urinary sphincter muscles;

(d) issuing verbal instructions by means of the computer to the effect that said person should hold the urinary sphincter muscles in the contracted state;

(e) issuing verbal instructions by means of the computer to the effect that said person should let go, i.e., release, said person's urinary sphincter muscles;

(f) repeating steps (c) through (e) a plurality of times;

(g) verbally rewarding said person by means of the computer for having performed the method;

(h) upon initiation of the therapeutic method, filling a scoreboard with an array of visible indicia;

(i) sequentially reducing the size of the array in an inwardly contracting fashion during steps (c) and (d) to simulate the contraction of the sphincter muscles; and (j) sequentially increasing the size of the array in an outwardly expanding fashion during step (e) to simulate the release of the sphincter muscles.

19. A second therapeutic treatment method for practice by said person under treatment to strengthen said person's urinary sphincter muscles, increase awareness of a full bladder, and to increase bladder capacity, comprising the steps:

(a) keying a computer to initiate said method at least once a day when said person under treatment feels the need to urinate, said computer being adapted to create humanly audible sound at least in the form of synthesized speech;

(b) verbally acknowledging to said person by means of the computer that said person is feeling a need to go to the bathroom to urinate;

(c) initially clearing a scoreboard of visible indicia under control of the computer, said scoreboard having an array of cells arranged in rows and columns, each cell containing centrally therein an indicium which can be selectively made visible and invisible by the computer;

(d) issuing verbal instructions by means of the computer to the effect that said person should refrain from going to the bathroom as long as said person can or until the scoreboard is full of visible indicia, then go to the bathroom and actuate a remote keying means which transmits a signal to the computer when actuated;

(e) periodically adding by means of the computer a visible indicium to the scoreboard at a corner of the scoreboard and advancing previously added visible indicia cell by cell and row by row across the scoreboard such that, after a number of periods equal to the number of scoreboard cells, the scoreboard will be full of visible indicia; until either the computer receives a transmission from the remote keying means or the scoreboard is full;

(f) if the scoreboard becomes full of indicia, congratulating said person and issuing verbal instructions by means of the computer to the effect that said person should go to the bathroom and actuate the remote keying means; and (g) upon actuation of the remote keying, maintaining the indicia configuration of the scoreboard long enough to enable said person to return to the computer and see how well he did.

20. The method according to claim 19 further comprising the steps: each time said person is able to fill the scoreboard, remembering that fact, and the next time said person practices the method, increasing the time it takes to fill the scoreboard to provide an increased challenge for said person up to a safe limit.

* * * * *